(12) United States Patent
Patton

(10) Patent No.: US 7,704,457 B2
(45) Date of Patent: Apr. 27, 2010

(54) AUTOMATIC, FIELD PORTABLE ANALYZER USING DISCRETE SAMPLE ALIQUOTS

(76) Inventor: Charles J. Patton, 6771 Brook Forest Dr., Evergreen, CO (US) 80439

( * ) Notice: Subject to any disclaimer, the term of this patent is extended or adjusted under 35 U.S.C. 154(b) by 610 days.

(21) Appl. No.: 11/599,571

(22) Filed: Nov. 14, 2006

(65) Prior Publication Data
US 2007/0116601 A1    May 24, 2007

Related U.S. Application Data

(60) Provisional application No. 60/737,933, filed on Nov. 18, 2005.

(51) Int. Cl.
| | |
|---|---|
| G01N 21/00 | (2006.01) |
| G01N 31/00 | (2006.01) |
| G01N 21/64 | (2006.01) |
| G01N 35/00 | (2006.01) |
| G01N 35/08 | (2006.01) |

(52) U.S. Cl. .............. 422/63; 422/67; 422/81; 422/82.05; 422/82.07; 436/43; 436/52; 436/55; 436/164; 436/172; 436/180

(58) Field of Classification Search .......... 422/81, 422/67, 63, 68.1, 82.05, 82.07, 82.08; 436/43, 436/52, 55, 161, 164, 168, 172, 180
See application file for complete search history.

(56) References Cited

U.S. PATENT DOCUMENTS

| | | | |
|---|---|---|---|
| 3,479,141 A | 11/1969 | Smythe et al. ............... 23/230 |
| 4,224,033 A | 9/1980 | Hansen et al. ............ 23/230 R |
| 4,253,846 A | 3/1981 | Smythe et al. ............ 23/230 R |
| 4,520,108 A | 5/1985 | Yoshida et al. ............... 436/52 |
| 4,774,190 A * | 9/1988 | Weiss ......................... 436/161 |
| 4,853,336 A | 8/1989 | Saros et al. ................... 436/53 |

(Continued)

FOREIGN PATENT DOCUMENTS

EP    0 088 440 A2    9/1983

(Continued)

OTHER PUBLICATIONS

Vieira et al., A Versatile Set Up for Implementing Different Flow Analysis Approaches Spectrophotmetric Determination of Nickel in Steel Alloys, Microchemical Journal, New York, NY, US, vol. 82, No. 1, Jan. 2006, pp. 56-60.

(Continued)

*Primary Examiner*—Brian R Gordon
(74) *Attorney, Agent, or Firm*—Michael W. Ferrell

(57) ABSTRACT

An automated apparatus and method for analyzing liquid samples by forming discrete sample aliquots (boluses) in an elongated conduit which contains a hydrophobic carrier liquid. Aliquots may be analyzed by adding at least one reagent to the sample aliquot that reacts selectively with an analyte contained therein. The reaction product, which is selective for the analyte of interest and proportional to its concentration, is measured with an appropriate detector. Intrinsic sample properties of the sample may also be measured without the need for adding chemical reagents. The invention enables simple and accurate testing of samples using time honored wet-chemical analysis methods in microliter volume regimes while producing remarkably small volumes of waste.

19 Claims, 17 Drawing Sheets

U.S. PATENT DOCUMENTS

| | | | |
|---|---|---|---|
| 5,149,658 A | 9/1992 | Cassaday et al. | 436/53 |
| 5,268,147 A | 12/1993 | Zabetakis et al. | 422/82 |
| 5,399,497 A | 3/1995 | Kumar et al. | 436/53 |
| 5,783,740 A | 7/1998 | Tawarayama et al. | 73/19.1 |
| 6,613,579 B2 | 9/2003 | Wolcott | 436/178 |
| 6,623,971 B2 | 9/2003 | Adolfsen | 436/53 |
| 7,129,091 B2 * | 10/2006 | Ismagilov et al. | 436/34 |
| 2005/0244299 A1 | 11/2005 | Dasgupta et al. | 422/68.1 |
| 2006/0020427 A1 | 1/2006 | Kahn et al. | 702/188 |
| 2006/0172425 A1 | 8/2006 | Neigl et al. | 436/18 |
| 2007/0062583 A1 * | 3/2007 | Cox et al. | 137/565.01 |

FOREIGN PATENT DOCUMENTS

| | | |
|---|---|---|
| EP | 0 562 260 A2 | 9/1993 |
| GB | 2 192 278 A | 1/1988 |
| WO | WO 2005/059512 | 9/2005 |

OTHER PUBLICATIONS

Tiggelaar et al., Analysis Systems for the Detection of Ammnia Based on Micromachined Components Modular Hybrid Versus Monolithic Integrated Approach, Sensors and Actuators B, Elsevier Sequoia S.A., Lausanne, CH, vol. 92, No. 1-2, Jul. 1, 2003, pp. 25-36.

Jannasch et al., Submersible, Osmotically Pumped Analyzers for Continuous Determination of Nitrate in Situ, Analytical Chemistry, American Chemical Society, vol. 66, No. 20, Oct. 15, 1994, Columbus, US, pp. 3352-3361.

"Capsule Chemistry Technology for High-Speed Clinical Chemistry Analyses", Michael M. Cassaday, et al., Clinical Chemistry, vol. 31, No. 9, 1453-1456 (1985).

Autonomous Environmental Water Quality Monitoring—The Future of Continuous Flow Analysis, C.J. Patton, Environ. Chem., 2006, 3, pp. 1-2.

* cited by examiner

AUTOMATIC, FIELD PORTABLE ANALYZER USING DISCRETE SAMPLE ALIQUOTS

CLAIM FOR PRIORITY

This application is based upon U.S. Provisional Patent Application No. 60/737,933 entitled "Apparatus and Method for Automated, Field Portable Wet Chemical Analysis" filed on Nov. 18, 2005. The priority of U.S. Provisional Patent Application No. 60/737,933 is hereby claimed and its disclosure is incorporated into this application in its entirety by reference.

TECHNICAL FIELD

The present invention relates generally to a method and apparatus for measuring analytes in discrete aqueous aliquots. More specifically, the automated analyzer of the invention is adapted to analyze microliter sized aliquots, such that the analyzer may be placed, for example, at a remote location for monitoring water quality. Other fields of application may also be suitable for use with the invention, including industrial process monitoring and bioreactor monitoring.

BACKGROUND OF THE INVENTION

Automated analytical devices and methods capable of performing chemical assays on a series of samples are known in the art. Such devices enable fast, continuous, and reliable analysis of samples for a wide variety of analytes. One type of prior art device includes continuous flow devices which employ polymeric analytical conduits made from TEFLON®, where the conduits include silicone or fluorocarbon oils to preferentially wet the conduit or dispenser surfaces. The use of these materials was found to greatly minimize cross contamination (carryover) of aqueous analytical fluids or streams. These techniques—so called "oil patent" prior art were developed in the mid 1970's and are directed at minimizing sample and reagent cross contamination (carryover) in discrete dispensing operations or continuously flowing streams for high-speed clinical diagnostic testing.

Competing analytical systems, such as those which robotically dispense sample and reagent into various microtiter plate formats and so-called discrete random access clinical analyzers, are also known in the art. These types of systems operate on similar or smaller volume scales at even faster analysis rates and are essentially free of carryover provided that dispensing probes and stirring blades are thoroughly washed between dispensing operations. Because of these advantages, systems of this type have largely supplanted devices based on the "oil patent" technology in commercial applications.

Following is a brief summary of various automated analytical apparatuses and methods described in the art.

U.S. Pat. No. 3,479,141 to Smythe et al. discloses an automated analytical apparatus which transports a plurality of aqueous samples down a flowing stream to a photodetector. The liquid samples may be separated by air segments. According to Smythe et al. inter-sample contamination is successfully reduced by employing a TEFLON® conduit tube, and a liquid carrier medium which is inert and immiscible with the samples. Silicone oil is given as a suitable non-aqueous carrier medium.

In an article entitled "Capsule Chemistry Technology for High-Speed Clinical Chemistry Analyses" by Michael M. Cassaday, et al., *Clinical Chemistry*, vol. 31, no. 9, 1453-1456 (1985), a continuous flow analytical technique is described where a plurality of micro-aliquots of sample and various reagents are formed in a conduit in the presence of a liquid perfluorocarbon medium. Each sample and reagent micro-aliquot is separated by an air bubble. The presence of the air bubble and the perflourcarbon medium reportedly reduce unwanted sample and reagent carryover. Adjacent micro-aliquot capsules of sample and reagent(s) may be combined to initiate chemical reactions by expanding the diameter of the conduit in a "vanish zone," so-called because it is designed to remove the air barrier between the capsules allowing the adjacent aliquots to mix. The aliquots then continue through the conduit to a series of in-line reaction detectors, e.g. colorimetric, which are used to quantify the amount of an analyte in a given sample.

U.S. Pat. No. 5,149,658 to Cassaday et al. discloses a method for providing a plurality of discrete samples in a continuous flow analyzer, where the sample aliquots are separated by air and a fine layer of immiscible isolation liquid. The separated samples thus described flow through a conduit which has a sampling probe displaced in the center of the conduit which essentially serves to decrease the amount of isolation liquid separating the samples, yet maintain discrete sample aliquots.

Similar technology is described in PCT International Publication No. WO2005/059512 to Applicant Northeastern University, which relates to a continuous flow analyzer or other microfluidic devices, which can transport a plurality of discrete sample boluses into a micro NMR coil. The device includes a transfer conduit which has an immiscible carrier liquid to prevent the sample bolus from wetting, and thereby contaminating the conduit.

U.S. Pat. No. 4,853,336 to Saros et al. relates to a system of mixing liquid samples with reagents and diluents in a continuous flow analyzer. Similar to the Cassaday publication, the Saros et al. patent is stated to be useful in analytical systems where multi-stage reactions are required. The Saros et al. reference forms discrete sample/reagent section that are separated by air bubbles, where the sample aliquots may be later mixed with additional reagent aliquots by sending the stream through a "vanish zone."

U.S. Pat. No. 6,623,971 to Adolfsen describes a similar configuration for magnetic particle stat immunoassays. Specifically, as seen in FIG. 4 of the '971 patent, a sample package containing magnetic particles is separated from additional reagents by air bubble and wash aliquots. A magnet transfers the magnetic particles to the additional reagent components which causes photons to be emitted in proportion to the analyte concentration in the sample; the emission is measured by a luminometer. According to the '971 Adolfsen patent, optical carryover between samples is reduced by including a quench package, Q, which terminates the luminescent reaction.

U.S. Pat. No. 5,399,497 to Kumar et al. relates to an automated capsule chemistry system whereby sample packages and reagents are separated by air bubbles and subsequently mixed in a vanish zone. The '497 Kumar et al. reference employs bidirectional pumps such as syringe pumps to aspirate the sample packages and introduce them into the analytical conduit. Similar techniques and devices are also described in U.S. Pat. No. 5,268,147 to Zabetakis et al. and United States Patent Application Publication No. 2006/0172425 to Neigl et al.

Additional references of interest include U.S. Pat. No. 6,613,579 to Wolcot, U.S. Pat. No. 4,520,108 to Yoshida et al, and U.S. Pat. No. 4,224,033 to Hansen et al.

The above approaches, while suitable for analytical operations in medical diagnostics and the like, are impractical for other purposes. For example, the above described techniques require highly complex robotic arms which are used to aspirate the sample and reagent at the tip of the sample needle.

There accordingly exists a need for an automated analytical system that is simple and operable by non-experts, which has low power requirements, and generates small waste volumes—significant hurdles to making an analytical device portable.

Specifically, in the spheres of environmental, industrial, and bioreactor monitoring, there is increasing demand for chemical measurements obtained at higher temporal resolution than can be economically achieved by manual sample collection followed by laboratory analyses. These assessment needs could be met with automatic instrumentation installed at remote locations or in production plants, provided that they were affordable, easy to operate and maintain, and produced data on a par with analytical laboratory results. Typically, in these settings sampling rates of about four per hour to one per day are needed. Sensor technology for water quality parameters such as dissolved oxygen have been improved greatly over the past five years, but progress on sensors for other analytes such as ammonium, nitrate and orthophosphate has been less fruitful. For this reason, most successful automatic water quality monitors still rely on wet-chemical analyses with colorimetric or fluorimetric detection. The cost and complexity of conventional field portable chemical analyzers currently limit their use. Furthermore, the need to replace reagents, perform calibrations, and manage the resulting analytical waste stream has proved particularly problematic for non-specialist operators.

It has been discovered according to the present invention that the above objects can be accomplished by providing an automated analytical system where microliter-sized liquid sample aliquots are introduced into the system and may be positioned to receive various reagents from a dosing module as needed. After the reagent and sample react for the desired time, the aliquot can be positioned to receive additional reagents if needed, or may be conveyed to a detection zone where it is measured for analyte. The apparatus and method described herein enable time-honored wet chemical analyses to be performed on a microliter volume scale with sensor-like simplicity. The apparatus and method further address and solve heretofore intractable problems related to field monitor and industrial process monitor operation and maintenance, power requirements, and waste stream management.

Among other advantages, the present invention (1) is simple and may be operated by non-experts; (2) has very small reagent requirements; (3) generates little waste volume; (4) is virtually immune to optical window fouling; (5) has low electrical power requirements; and (6) is cost effective. Furthermore, it is ideally suited for environmental and process monitoring, and can be made field portable or production-floor portable. These and other features and capabilities of the invention will be made clear in the description which follows and with reference to the accompanying drawings.

SUMMARY OF THE INVENTION

In one aspect of the present invention an automated analyzer is provided to analyze discrete sample aliquots, where the analyzer includes (a) an analytical conduit containing hydrophobic carrier fluid, where the conduit is suitable to receive liquid aliquots of predetermined volume which are essentially immiscible with the hydrophobic carrier fluid; (b) a pump located at a first position with respect to the conduit and communicating with the carrier fluid such that it is operative to induce controlled flow of the fluid in the conduit in response to a first control signal; (c) a shut-off valve located at a second position with respect to the analytical conduit, and being operative to prevent flow of the carrier fluid at the second position; (d) a dosing unit located at a third location with respect to the analytical conduit, being intermediate to the first and second locations, where the dosing unit has a reservoir configured for communicating with the conduit through a feed valve that is responsive to a third control signal; a controller providing the first, second, and third control signals, respectively to the pump, shut-off valve, and feed valve, whereby the pump may be used to draw fluid from the reservoir by concerted operation of the pump, shut-off valve, and feed valve; and (f) a detector located at a fourth position with respect to the conduit and operable to detect an analyte in the discrete immiscible aliquot.

In another embodiment of the invention, there is provided a method for analyzing discrete liquid aliquots including the steps of introducing a discrete liquid aliquot into an analytical conduit which includes a hydrophobic carrier fluid; using a pump that is in communication with the analytical conduit to position the discrete liquid sample in the analytical conduit to receive at least one reagent from a dosing unit; and measuring the liquid aliquot with a detector to quantify the amount of analyte that is present in the aliquot.

Still further features and advantages of the invention are apparent from the following description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is described in detail below with reference to the following drawings.

DETAILED DESCRIPTION OF THE INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning.

According to the invention, an apparatus and method are provided that enables the automated analysis of discrete liquid samples using wet chemical reagents to detect analytes. The discrete samples analyzed with the invention, and the reagents used, are generally aqueous, although samples/reagents having other polar solvent media may be used as well, e.g., methanol, ethanol, mixtures of water and alcohols, and the like. "Aqueous" as used herein, means having at least 50 weight percent water. According to the invention, a small-volume discrete liquid sample (also referred to herein as an "aliquot" or "bolus") is formed in an analytical conduit which contains a hydrophobic carrier liquid. The discrete sample that is formed should be essentially immiscible with the hydrophobic carrier liquid, e.g., generally having a solubility therein of less than about 500 ppm. The discrete sample is then sequentially treated with appropriate colorimetric, nephelometric, or fluorometric derivitizing reagents by the coordinated operation of a precision pump, a dosing module, and a shut-off valve along the analytical conduit. Additionally, intrinsic properties of the sample bolus may be measured, i.e., where chemical reagents are not added to the bolus prior to detection. For example, native fluorescence may be measured to determine chlorophyll concentration in water, and UV absorbance may be measured to determine nitrate concentration.

Figure 1:
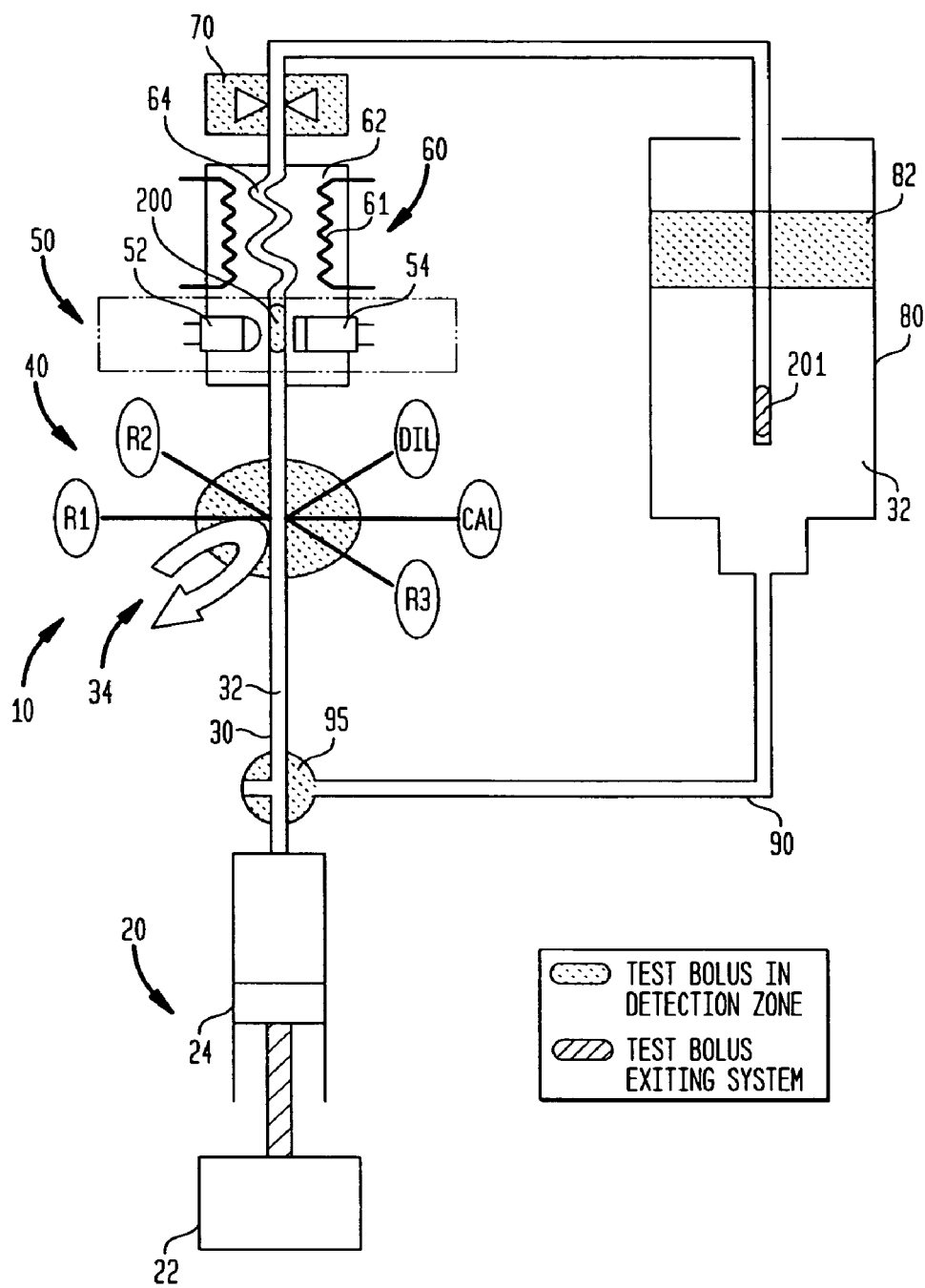
FIG. 1 is a schematic diagram illustrating an automated analytical device of the invention.

The invention is illustrated with reference to the embodiment shown in FIG. 1 which is a schematic diagram of an automated analytical device. There is provided an automated analytical apparatus 10 which includes a precision pump unit 20 comprising a stepper motor 22 connected to a piston or plunger on syringe 24. The syringe is in communication with analytical conduit 30 which is filled with a perfluorocarbon carrier fluid 32 (also sometimes referred to as "carrier liquid," "system fluid" or the like). A sampling unit 34 is positioned along the analytical conduit as a discrete module or incorporated into the doser module as shown in FIG. 1. The sampling unit 34 is configured to provide discrete sample aliquots to the analytical conduit from a sample source. There also includes a dosing module 40 which comprises dosing units for three reagents, R1, R2, and R3, as well as dosing units to dispense diluent, DIL, and a calibration standard, CAL. The number of different fluids that can be introduced successively into the analytical conduit, with reaction periods in between, is limited only by the number of dosing units on the dosing module. The derivitizing agents or reagents used in the invention are typically provided as aqueous solutions. The dosing module may be configured in a circular array around the longitudinal axis of the analytical conduit, linearly along the longitudinal axis of the analytical conduit, or any other suitable configuration.

The apparatus includes a mixing/heating unit 60 having a conductive heating block 62, e.g. an aluminum block, resistive heating elements 61 and a mixing zone 64 formed by coiling or figure-eight looping the analytical conduit tubing. In operation, a sample/reagent aliquot may be positioned in the heating unit to increase reaction kinetics, and may be passed back and forth in the mixing zone to homogenize combined aqueous solutions. It may be useful to park the bolus in the heated zone in order to provide a controlled temperature environment in which the reagent/analyte reaction proceeds. In this regard, inconsistencies or errors associated with variations in ambient temperature of the analyzer may be minimized.

A shut-off valve 70 is positioned on analytical conduit 30 which, when in a closed position, is operative to prevent fluid flow therethrough. The shut-off valve is generally a 2-way, normally closed valve, e.g a check valve. A normally open valve may be used as the shut-off valve as well. According to the invention, the flow through the analytical conduit may be controlled to introduce samples, reagents, diluents, or other components; details of the control scheme are provided hereafter.

The analytical device includes a detection zone 50, which, in this embodiment, has a light emitting diode (LED) 52 and a photodiode (PD) 54. In most photometry and fluorimetry applications, an interference filter will be included in front of the photodiode for wavelength discrimination. The discrete sample aliquot 200, for example a water sample, containing one or more derivitizing reagents, may be positioned in the detection zone where generally the LED/PD detector will measure absorbance at a given wavelength to quantify the amount of analyte in a sample. It is generally preferred that the analytical conduit and, therefore, the bolus, are configured in a vertical position in the detection zone. This is advantageous because any small air bubbles that inadvertently enter the bolus from reagent or sample outgassing will float upwardly in the bolus and out of the light path. Additionally, any suspended sediment in the bolus will sink downwardly out of the light path, preventing light scattering that may occur if the analytical channel was not oriented vertically.

The analyte may be quantified by referencing the absorbance of the sample to a calibrated absorbance curve of analyte standard. Various measurements including colorimetric, nephlorimetric, or fluorimetric measurements may be made radially through the analytical conduit cross section. When the aqueous test bolus 200 crosses the light path of the detector it is easily detected in the system fluid from the light scattering of the sample's proximal or terminal meniscus. The test bolus may be parked in the detection zone by stopping the flow through the analytical conduit 30. Depending on the analytical requirements of the test method, the detector may consist simply of a light emitting diode (LED) and a photodiode (PD) mounted in opposition—180° for photometry; 90° for fluorimetry; some other oblique angle for nephlorometry—to the radius of the analytical conduit as suggested by dotted-line portion around the detection zone in FIG. 1.

Figure 2:
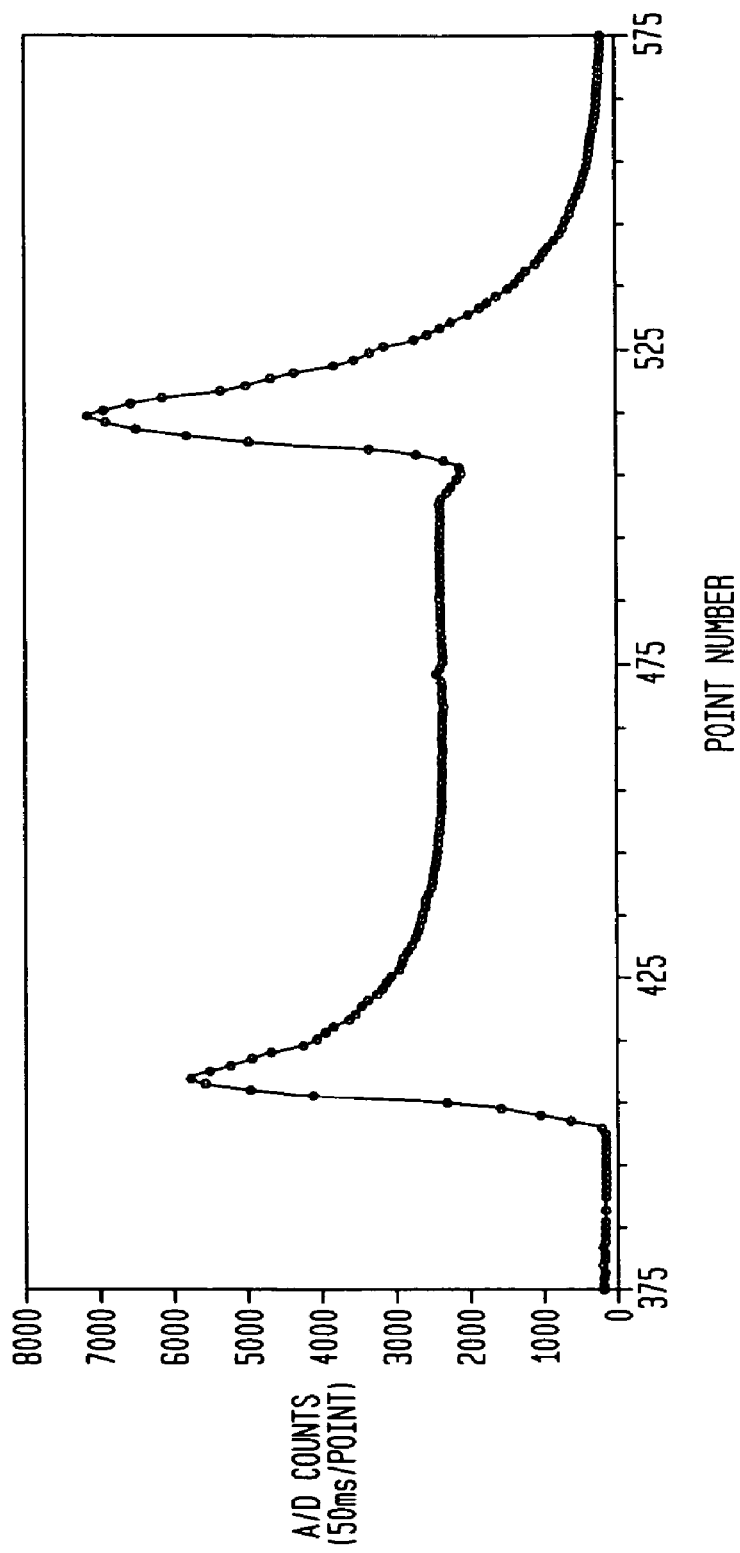
FIG. 2 is a graph showing the absorbance when measuring Griess reaction nitrite in a discrete test bolus prepared according to the invention, where the bolus is flowing past the photometric detector module.

FIG. 2 is a graph depicting a scan of an aqueous aliquot sample for nitrite detected by subjecting a sample bolus to the Griess reaction. The nitrite in the sample is present in a concentration of about 0.25 mg-N/L. In FIG. 2, the end spikes with maxima near points 405 and 515 define the terminal ends, or menisci, of the discrete test bolus. The absorbance in the center portion is proportional to the nitrite concentration in the bolus. Furthermore, as can be seen in this example, the test bolus has a fairly uniform concentration of detectable analyte across its length.

The concentration of nitrite in a sample bolus may be determined with reference to a standard calibration curve. The standard calibration curve can be prepared by diluting a standard calibration solution to produce a series of standard boluses having a known concentration of analyte and plotting the absorbance versus concentration. For example, Table I below outlines data taken to produce a standard calibration curve of nitrite analyte using 60 µL boluses produced in triplicate. The analyte was measured using a green LED as the light source and a photodiode equipped with an integral 543 nm interference filter as the detector in the configuration shown in FIG. 1.

TABLE 1

| Std. Conc. (mg/L) | Bolus Series #1 | | Bolus Series #2 | | Bolus Series #3 | | Avg Abs. |
|---|---|---|---|---|---|---|---|
| | A/D count | Abs. | A/D count | Abs. | A/D count | Abs. | |
| 0.00 | 21339 | 0.0000 | 21297 | 0.0000 | 21346 | 0.0000 | 0.0000 |
| 0.05 | 20298 | 0.0217 | 20325 | 0.0203 | 20273 | 0.0224 | 0.0215 |
| 0.10 | 19236 | 0.0451 | 19278 | 0.0433 | 19252 | 0.0448 | 0.0444 |
| 0.15 | 18300 | 0.0667 | 18337 | 0.0650 | 18319 | 0.0664 | 0.0660 |
| 0.30 | 15827 | 0.1298 | 15877 | 0.1275 | 15874 | 0.1286 | 0.1287 |
| 0.60 | 12100 | 0.2464 | 12173 | 0.2429 | 12190 | 0.2433 | 0.2442 |
| 0.90 | 9641 | 0.3451 | 9698 | 0.3416 | 9742 | 0.3407 | 0.3425 |

Figure 3:
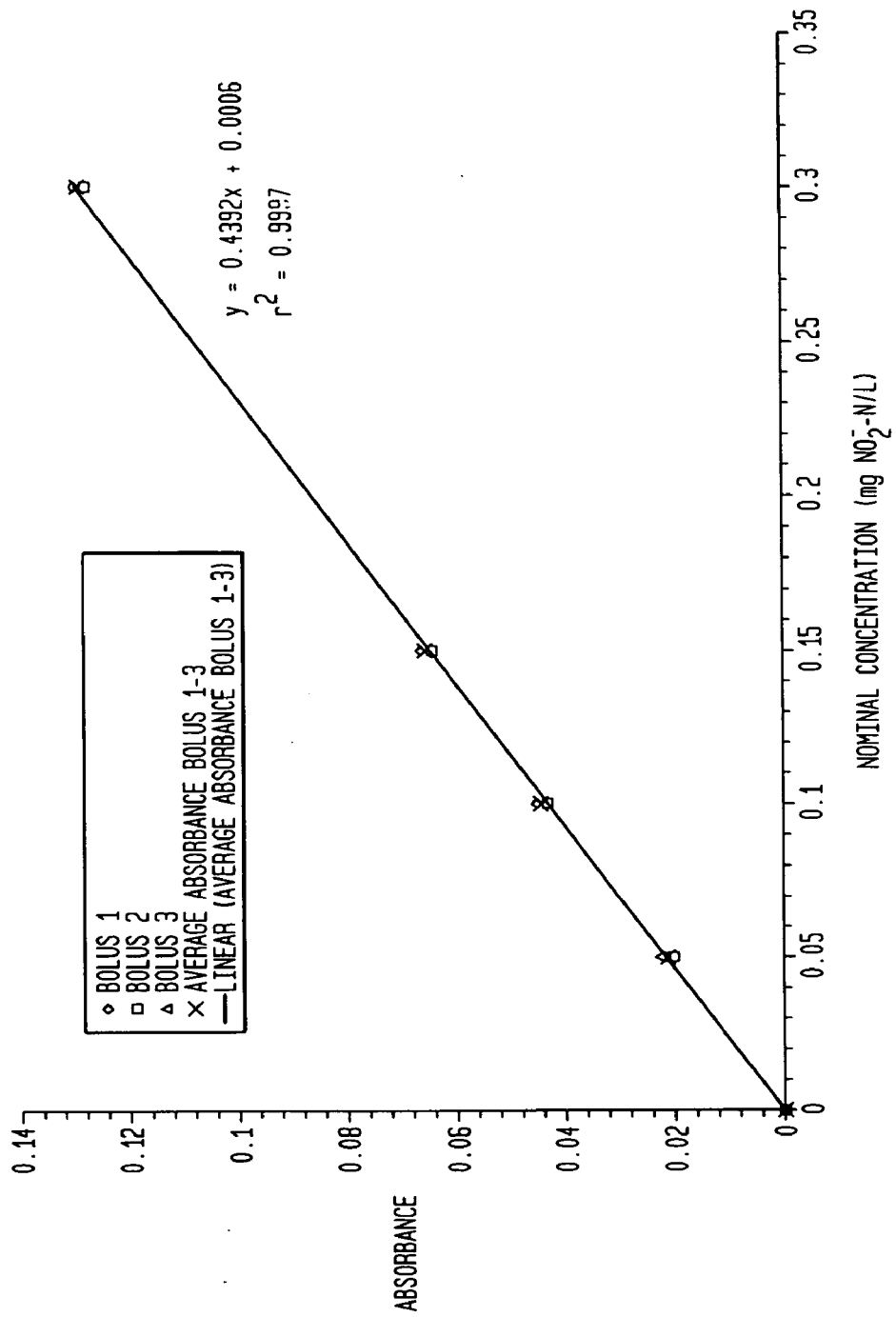
FIG. 3 is a graph showing a standard calibration curve which relates Griess Reaction chromophore absorbance to the concentration of nitrite.

The nitrite calibration data above produced a substantially linear calibration curve at lower concentrations (up to 0.3 mg/L), which is shown graphically in FIG. 3. The data taken from 0 to 0.9 mg-N/L nitrite also produces a substantially linear curve, though it more accurately defines a 2nd order polynomial curve.

After the measurement is complete, the pump pushes the analyzed sample bolus 201 (referring again to FIG. 1) out of the analytical conduit 30 and into the carrier fluid/waste receptacle 80. The outlet of the analytical conduit is positioned below the surface of the hydrophobic system fluid to avoid aspiration of air into the conduit. Here, as less dense aqueous test boluses, e.g. 201, exit analytical conduit 30, they rise through the immiscible carrier fluid 32 and form an aqueous waste layer 82 above it. The denser carrier fluid 32 is intermittently accessed from the bottom of receptacle 80 and recycled into the analytical conduit during syringe pump refill cycles via recycle conduit 90. To this end, the pump is alternately connected to the analytical conduit or the system fluid reservoir by appropriate actuation of an integral 3-way valve 95 as shown in FIG. 1. Recycling the system fluid allows operation for extended periods without replenishment.

The method of operating the sampling unit and dosing units are illustrated in greater detail with reference to FIGS. 4a through 4g. In FIGS. 4a-4g the dosing aspect of the invention is shown in an embodiment which has several dosing units for reagent or diluent addition along the analytical conduit 30. The analytical conduit 30 comprises polymeric tubing and an inert, perfluorocarbon carrier liquid 32. The analytical conduit typically has an inside diameter in the range of from 1 to 3 mm. As noted above, the use of a fluorocarbon polymeric tubing material, such as TEFLON®, with a perfluorocarbon carrier liquid is preferred, because it aids in preventing substantial carry-over contamination between subsequent aqueous samples due to the ability of the perfluorocarbon carrier liquid to wet the inner walls of the hydrophobic TEFLON® tubing. This enables an apparatus that produces remarkably small waste volumes because inter-sample wash liquids are generally not needed to prevent contamination. It is contemplated in connection with the invention, however, that other tubing/carrier liquid combinations may be used. The arrow at the left of each drawing in FIGS. 4a-4g indicates the pump flow direction at each sequence, where a left arrow represents reverse fluid flow (piston retracting), and a right arrow represents forward fluid flow (piston inserting).

Figure 4A:
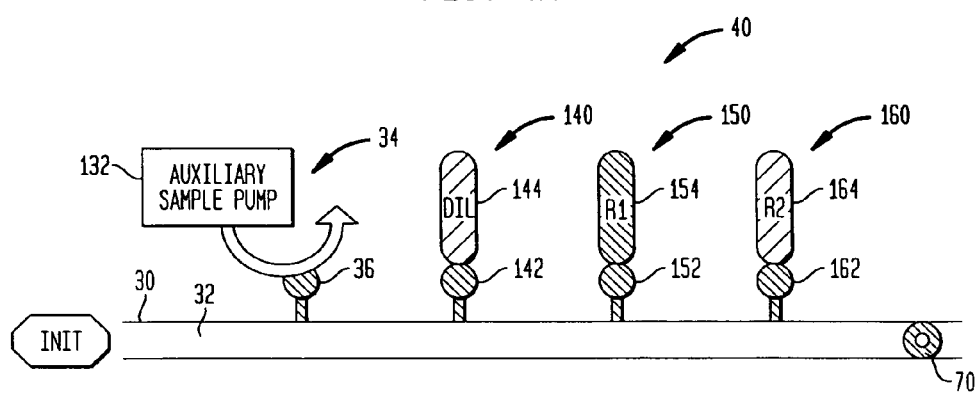
FIG. 4*a*-4*g* are schematic diagrams of an analytical conduit, sampling unit, and dosing module, which show the operation and control of the invention.

There is seen in the schematic of FIG. 4a, a sampling unit 34, a dosing unit 40, and normally closed, 2-way valve 70. The pump system, detection zone, and heater/mixer portion are omitted for clarity. In specific embodiments, the sampling unit 34 may be variously implemented with a 4-way rotary valve arrangement (shown in detail in FIG. 11), or with a 3-way solenoid valve, as suggested in FIGS. 1, 4a-g, and 8. Additionally, the sampling unit 34 may employ a 2-way normally closed (NC) solenoid valve with the normally closed port fitted with coaxial tubing, and configured such that the sample enters one leg of the coaxial tubing, flushes the void volume of the normally closed valve, and exits up the other leg of the coaxial tubing. The sampling unit generally includes an auxiliary pump 132 that is coupled to a sample source to transport aqueous sample to the analyzer. The sampling valve may be opened to the analytical conduit in order to draw a discrete sample bolus from the sample conduit, or may be opened to waste to flush the sampling unit, for example, prior to drawing a new sample to prevent cross-contamination from the previous sample. The dosing module 40 includes a diluent dosing unit 140, a first reagent dosing unit 150, and a second reagent dosing unit 160. Each dosing unit includes a two way feed valve indicated at 142, 152, and 162, respectively which controls the flow of liquid from the reservoir (144, 154, and 164 respectively). The analytical cycle begins in FIG. 4a with the analytical conduit 30 completely filled with a perfluorocarbon carrier liquid 32. Here again, the number of different fluids that can be introduced successively into the analytical conduit with reaction periods in between is limited only by the number of dosing units coupled to the conduit.

Figure 4B:
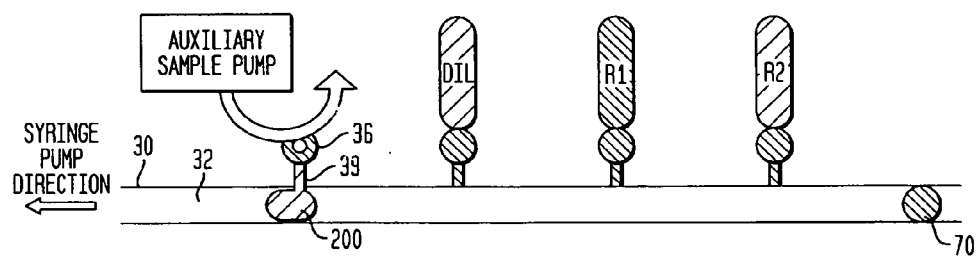
Figure 4C:
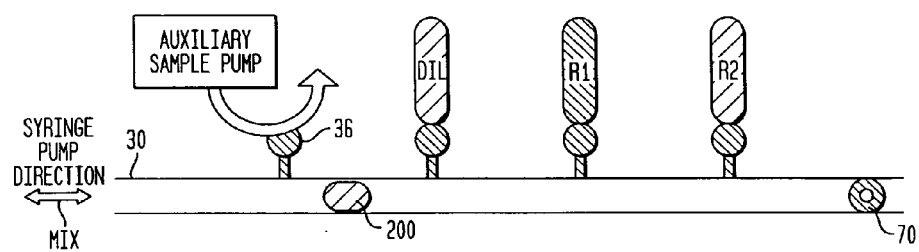

Referring to FIG. 4b, a discrete sample bolus 200 is formed in the analytical conduit 30 by closing the 2-way valve 70 and opening the 3-way sampling valve 36 to the analytical conduit. The piston on a syringe pump (not shown) is retracted, causing reverse fluid flow into the analytical conduit upstream from the sampling unit, and inducing a precise, programmed volume of sample to enter the analytical conduit via sampling conduit 39. In this regard, the pump is stepped until the desired volume of sample, e.g. 10 microliters, is aspirated into the analytical conduit in the form of a bolus. The pump is then turned off and the sampling valve is closed to the analytical conduit. As seen in FIG. 4c, once the discrete aliquot 200 is introduced into the analytical conduit 30, the 2-way valve 70 may be opened and the sample may be conveyed through the analytical conduit as desired by operating the syringe pump to control the flow through the conduit either in a forward (toward the shut-off valve 70) or reverse direction. If the dead volume in the normally closed section of the sampling valve 36 is significant, the first test bolus can be discarded by closing the sample valve 36, reopening the downstream shut-off valve 70, and actuating the syringe pump to push the bolus down stream and out to the waste.

Alternatively, in one preferred embodiment, after the sampling valve is flushed and charged with sample for the next sample (a new sample), the bolus from the previous test is positioned adjacent to the sampling port 39 (e.g. in the module in FIG. 11), and a volume of new sample sufficient to completely rinse the void volume of the sampling module is aspirated into the old test bolus which is then pumped to the waste. The rinse volume is about 2 to 10 microliters, typically about 5 microliters, and contributes minimally to the total waste generated by the apparatus, and leads to higher operating efficiency.

In some instances, it may be necessary to generate a bolus of diluent (typically deionized water) from dosing unit 140, and aspirate a small amount of sample into the diluent bolus. This may be done, for example, when it is needed to create a series of calibration standards from a single, more concentrated, calibration solution as described above in connection with the curve shown in FIG. 3. Additionally, the diluent dosing unit may be used to dilute a sample having analyte in a concentration that exceeds the calibration range.

Figure 5:
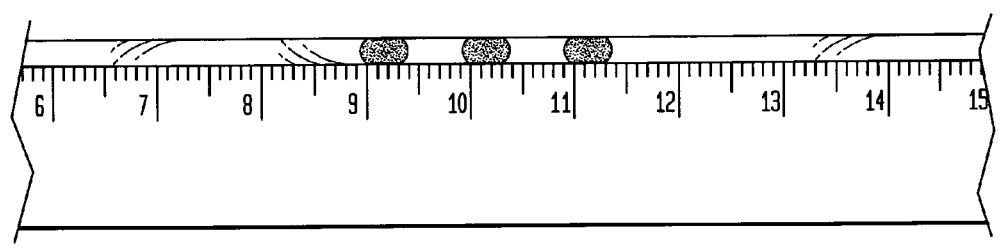
FIG. 5 is an illustration showing a series of discrete test aliquots produced according to the invention in a hydrophobic carrier liquid in an approximately 2 mm internal diameter TEFLON® conduit, where it is seen that the volume is highly reproducible.
Figure 6:
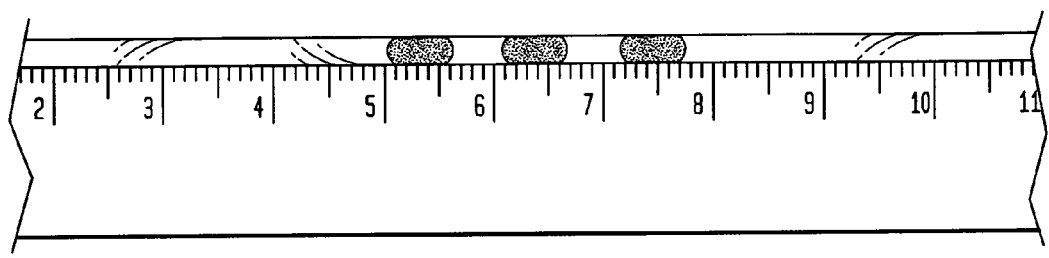
FIG. 6 is another illustration with a series of discrete test aliquots produced according to the invention in a hydrophobic carrier liquid in an approximately 2 mm internal diameter TEFLON® conduit, where it is seen that the samples are also reproducible at larger volumes.
Figure 7:
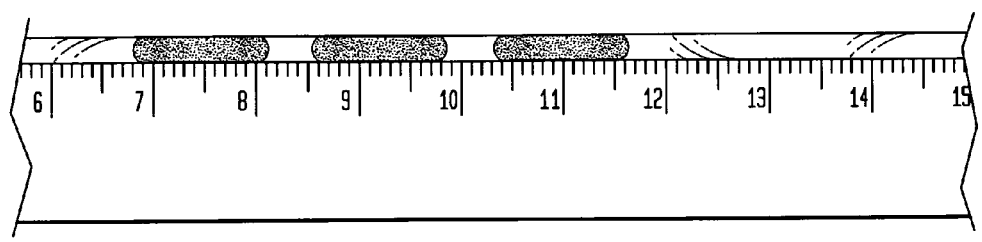
FIG. 7 is a third illustration of a series of discrete test aliquots produced according to the invention in a hydrophobic carrier liquid in an approximately 2 mm internal diameter TEFLON® conduit, where, again, larger volume samples also appear to be reproducible.

The discrete sample is generally formed at a volume of from about 1 to about 500 microliters, preferably from 1 to 100 microliters, 5 to 50 microliters, or from 10 to 30 microliters; however, for some applications larger volumes of about 500 microliters to 5,000 microliters may be used. A precision syringe pump enables the formation of discrete samples having different sizes, where the volumes of the samples are extremely reproducible. See, for example, FIGS. 5-7 which illustrate 3 boluses in a conduit, where the boluses are sized differently for each figure. FIGS. 5-7, which were prepared frpm photographs, show that the sample volume of the boluses is reproducible using the inventive technique, even over a large range of bolus volumes. Table 1, below outlines the minimum aqueous test bolus volume for stable flow in system fluid as a function of analytical conduit inside diameter ($d_1$).

TABLE 2

Relation of conduit diameter to bolus size

| Analytical conduit inside diameter ($d_t$, mm) | $V_{tube}$/cm (μL) | $V_{sphere}$ (μL) | $V_{slug}$ minimum (μL) | Slug length at $V_{min}$ (mm) |
|---|---|---|---|---|
| 0.50 | 1.963 | 0.065 | 0.115 | 0.586 |
| 1.00 | 7.854 | 0.524 | 0.920 | 1.171 |
| 1.50 | 17.671 | 1.767 | 3.105 | 1.757 |
| 2.00 | 31.416 | 4.189 | 7.360 | 2.343 |
| 2.50 | 49.087 | 8.181 | 14.375 | 2.928 |
| 3.00 | 70.686 | 14.137 | 24.840 | 3.514 |
| 5.00 | 196.350 | 65.450 | 115.00 | 5.857 |

In the above table, the minimum theoretical bolus volume needed to have stable flow in the analytical conduit is listed for a given conduit diameter, where $V_{sphere}$ is for spherical boluses and $V_{slug}$ is for capsule-shaped boluses. $V_{slug} \approx 0.92\, d_t^3$, where $d_t$=inside diameter of the tube. Capsule shaped boluses ($V_{slug}$) are preferred, because system fluid tends to flow around spherical boluses, rather than push or pull them as it does with capsule shaped aliquots. It should also be noted, that once a bolus with a volume equal to or greater than $V_{slug}$ minimum is formed in the analytical conduit, other liquid volumes (including those with volumes less than $V_{slug}$ minimum) may be aspirated into the bolus.

Figure 4D:
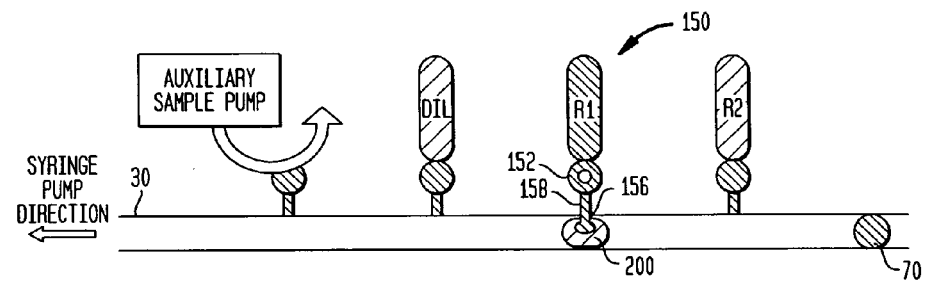
Figure 4E:
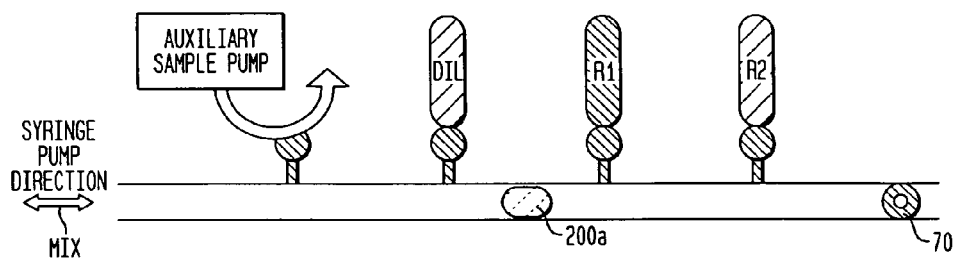
Figure 4F:
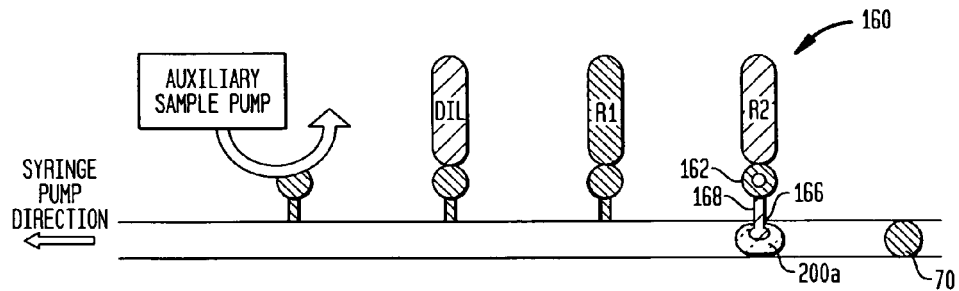

Referring now to FIG. 4d, the sample bolus 200 is positioned adjacent to dosing port 156 by controlling the flow through the analytical conduit 30. Valve 70 is closed, the 2-way valve 152 is opened on the reagent dosing unit 150, and the syringe piston is concurrently retracted to introduce reagent R1. Reagent R1 passes through the reagent conduit 158, out of dosing port 156 and is combined with the sample bolus 200. Here also, once the desired amount of reagent is introduced, the two way valve 152 is closed. To aid in sample uniformity, i.e., to thoroughly mix the reagent and the sample, the shut-off valve 70 may be opened, and the sample conveyed bi-directionally through the analytical conduit as seen in FIG. 4e. Optionally, this is done through a heating/mixing zone as is illustrated schematically in FIG. 1 until the desired delay time is reached. Typical delay times between successive reagent addition range from 1 second to 30 minutes; more preferably from 10 seconds to 10 minutes, or from 30 seconds to 5 minutes.

Figure 4G:
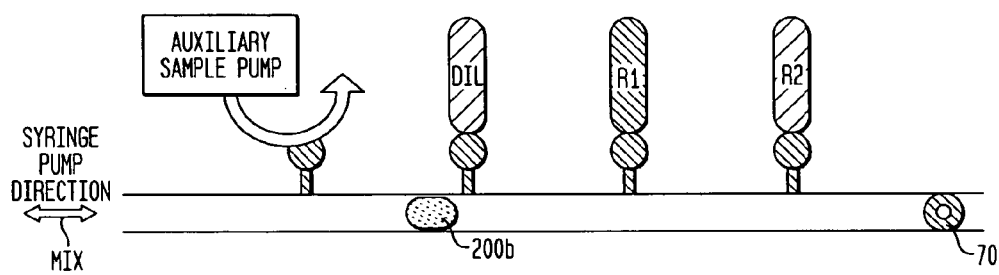

Once the first reagent and the sample have reacted for the desired amount of time, the sample 200a may be positioned adjacent to dosing port 166 (referring here to FIG. 4f), where reagent R2 is combined with the sample in the same manner as described above. That is, the valve 70 is closed, the 2-way valve 162 is opened, and the syringe piston is retracted to introduce the second reagent. As shown in FIG. 4g the valve 70 may be reopened, and the sample containing both reagents 200b, may be mixed in the analytical conduit to further sample uniformity and/or heated to increase reaction kinetics. Additional reagents may be added as needed in the same manner as described above. When the reaction has advanced as desired, the bolus may be positioned in a detection zone to measure the targeted analyte, as was described above in connection with FIG. 1, above.

As will be appreciated from FIGS. 1 and 4a-4g, the invention is suitably practiced by automating the control of the pump, shut-off valves, dosing valves, and sampling valves with a control system. The control system is not particularly limited and may include, for example, an analog control system, digital control system, or a microprocessor control system such as a desktop computer. The valves may be solenoid or rotary valves which may communicate with the control system. The pump suitably has a stepper motor as the drive mechanism which may be in communication with the control system. The pump and valves each respond to a signal from the control system, e.g. for a valve to open or shut, a pump to induce flow, etc. One or more of the signals may be a derivative of the other.

The inventive apparatus may be operated with relatively few and simple moving parts, which is a substantial improvement over the prior art. For example, unlike the simple solenoids and stepper motor used in the invention, many prior art designs generally utilize expensive and power consuming robotic arms to introduce sample, reagents, and air bubbles into the analytical conduit.

In preferred modes of operating the present invention, air bubble segments or gaps are preferably not intentionally introduced into the analytical conduit, i.e., it may be substantially free of air bubble segments, and preferably the analytical conduit is entirely filled with liquid. Due to the high accuracy of the syringe pump system, and the incompressibility of the all liquid system, the sample boluses may be precisely positioned to receive reagents, or be positioned in the detection zone with remarkable accuracy. The accuracy with which the sample may be positioned in the invention is unique over the prior art, which generally uses peristaltic pumps to propel samples forward through a conduit, and also to aspirate air segments between samples to prevent contamination and/or for operation with vanish zones. Air bubbles are further undesired for use in the invention because they may affect the accuracy of the assay, for example, by scattering light in the detection zone. Accordingly, the analytical conduit of the invention generally has no need for vanish zones, and typically the conduit has a cross-sectional area that is substantially uniform over its length, i.e. the cross-sectional area does not vary by more than about 10%. In some embodiments, however, it may be desirable to increase the analytical conduit diameter in the detection zone, in order to improve the sensitivity of the apparatus per Beer's law by increasing the length of the light path through the bolus.

Although the operation of the invention has been illustrated with respect to one sample bolus in FIGS. 4a-4g, the inventive apparatus has the capability of forming a plurality of sample boluses in the analytical conduit, and dosing/analyzing them sequentially. For example, it is convenient to provide a calibration dosing unit having a predetermined amount of analyte standard. A plurality of discrete samples having varying concentrations of the analyte standard may be formed, for instance by dilution with diluent from another dosing unit. The instrument may then be calibrated, for example, by measuring absorbance of each of the standardized samples, and calculating the corresponding calibration curve. See, e.g., FIG. 3. It may also be convenient to form multiple boluses of the same sample, and add a different reagent set to each bolus to measure several constituents serially.

Specific aspects of the automated apparatus, including additional embodiments of the individual components, are described in greater detail below in connection with the remaining drawings.

Figure 8:
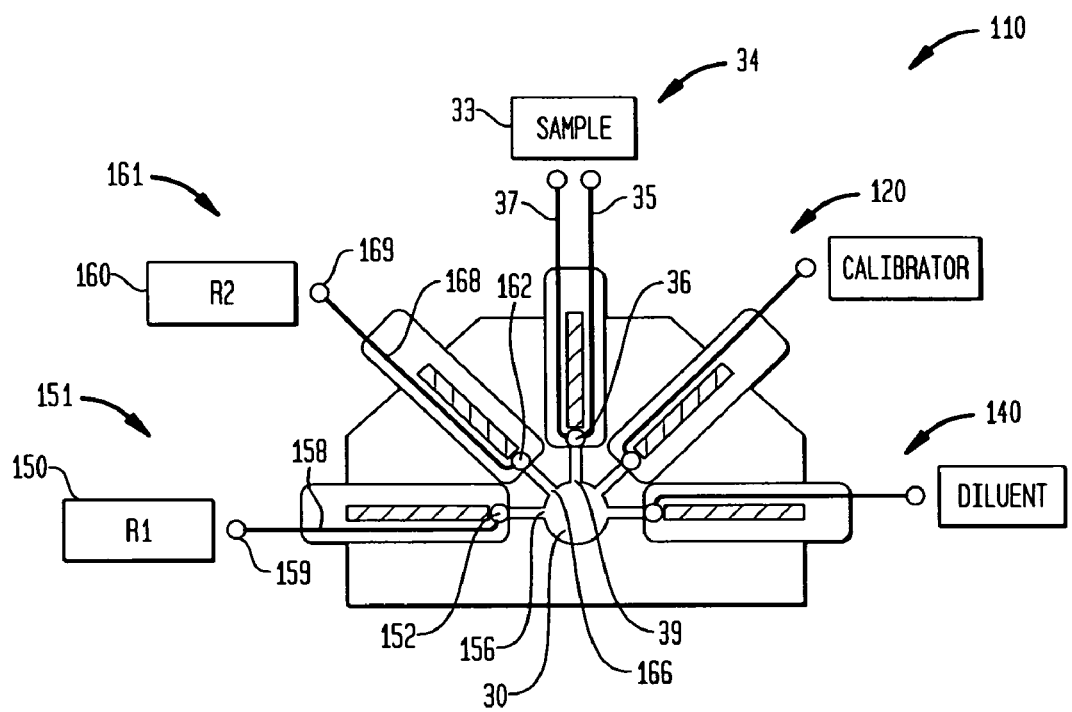
FIG. 8 is a schematic diagram showing the cross-sectional view of a solenoid valve actuated dosing module coupled to an analytical conduit.

FIG. 8 is a cross-sectional diagram of dosing module 110 based on a rotary array of solenoid valves that may be used in connection with the present invention. The rotary-array dosing module that comprises reagent dosing units 151, 161 which include reagent reservoirs R1 at 150, and R2 at 160. The reagents may enter analytical conduit 30 through dosing ports 156, 166 via reagent conduits 158 and 168. The two-way shut off valves on the reagent dosing units are indicated at 152 and 162 from their respective reagent reservoirs. Also shown are inlet ports 159 and 169 where the reagent is drawn into the reagent conduits. The dosing module 110 may also include a calibrator dosing unit 120 and diluent dosing unit 140 which include similar features as the reagent dosing units, such as dosing conduits, two-way valves, dosing ports, etc. In the embodiment illustrated in FIG. 8, the dosing module also includes a sampling unit 34, having a 3-way solenoid valve 36 which enables sample uptake from sample source 33, via sampling conduit 37. The sample enters the analytical conduit through sampling port 39. To flush the sampling conduit, the three-way valve may be closed to the analytical conduit, and the sample is allowed to flush through flushing conduit 35. A 2-way valve can also be used if coaxial tubing is connected to the normally closed port of the valve as previously described. In the embodiment shown in FIG. 8, the dosing units each have a dosing conduit and a dosing port which opens into the analytical conduit 30. However, in some embodiments, the dosing units may share a common dosing conduit and common dosing port. The use of a rotary dosing module may be desirable because they are more compact, and may not require as much transport of the sample boluses to add reagent.

Figure 9:
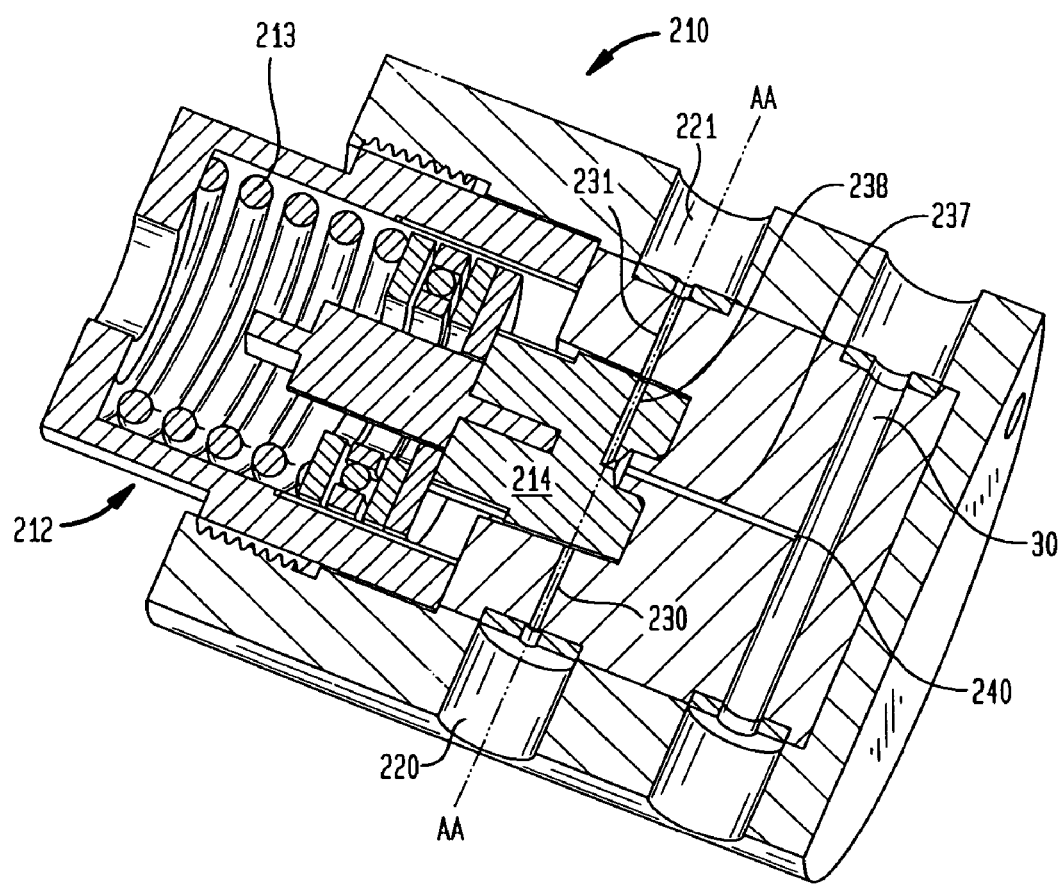
FIG. 9 is a cross-sectional view of an actuated rotary valve dosing module.

FIG. 9 illustrates a cross-section of a design of another rotary array dosing module 210 that may be used in the present invention. The rotary dosing module 210 includes a plug valve having a rotating stop cock 214 and drive mechanism (not shown). The valve also includes threaded collar 212 which retains compression spring 213 that "loads" rotating stop cock 214. The drive mechanism is typically a stepper motor, or perhaps, a rotary solenoid or rotary pneumatic actuator. The rotary dosing module is coupled to a plurality of dosing units, a portion of which are indicated at 220, 221. As shown in FIG. 9, each dosing unit includes a stationary dosing conduit 230, 231 which is positioned to contact a rotating dosing conduit 238 which is integrated in the rotating stopcock 214. The rotating dosing conduit 238 is coupled to a main dosing conduit 237 which opens up into analytical conduit 30 at dosing port 240. In operation, the rotating stop cock 214 may be controlled to selectively couple to each dosing unit via the stationary conduits, where each dosing unit may be operative to dispense reagent, diluent, hydrophobic carrier liquid, calibrant, sample, etc.

Thus, to activate a dosing unit (as in FIGS. 4a-4g), downstream valve 70 on the analytical conduit 30 is turned off and rotary stopcock 214 is positioned to be in fluid communication with dosing unit 221. When the piston on the syringe is retracted, liquid travels from the dosing unit 221 through the stationary reagent conduit 231 through the rotating dosing conduit 238, into the main dosing conduit 237, out of the dosing port 240, and into the analytical conduit 30.

Where other liquid components need to be introduced in the analytical conduit, e.g., additional reagents, carrier liquids, etc, the rotating valve is positioned such that the rotating dosing conduit 238 is positioned to contact another stationary dosing conduit, such as stationary conduit 230. In this design the dosing units share at least one common dosing conduit and a common dosing port. For this reason, it is preferred that one of the dosing units includes the hydrophobic carrier liquid which is present in the analytical conduit, such as the perfluorocarbon liquid. In preferred embodiments, after dispensing aqueous liquid from a dosing unit, the rotating stopcock is positioned to communicate with a dosing unit having a reservoir of the hydrophobic system fluid whereby the aqueous solution remaining in the void volume of the stopcock can be aspirated to the bolus, leaving the rotating dosing conduit 238 and main dosing conduit 237 filled with hydrophobic system fluid. The ability to clear the rotating dosing conduit part without aqueous rinsing is highly efficient and desirable, because a reagent, diluent, or reference solution will not be contaminated (commingled) with a previously aspirated solution.

Figure 10:
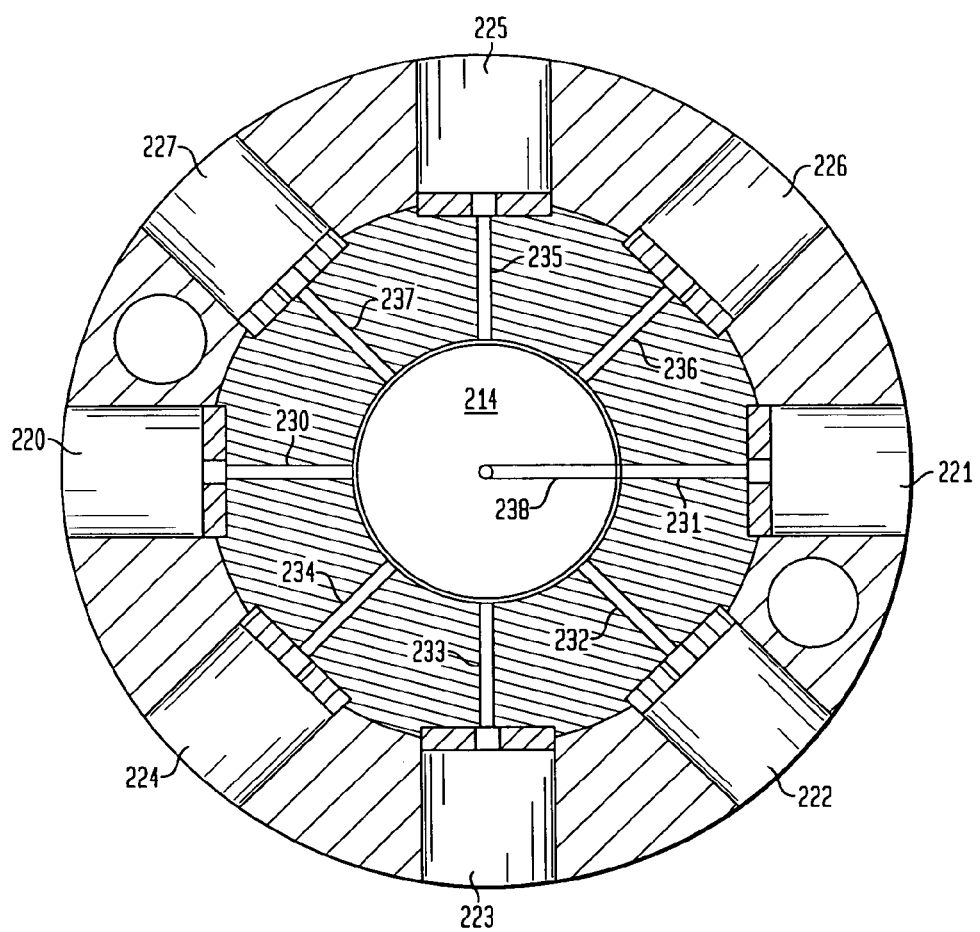
FIG. 10 is a cross-sectional view of the dosing module in FIG. 9 through line AA-AA.

The operation of the dosing module is further appreciated from FIG. 10 which is a cross-section of the dosing module in FIG. 9 through line AA. As can be seen in FIG. 10, the dosing module in this embodiment includes eight dosing units, portions of which are shown at 220, 221, 222, 223, 224, 225, 226 and 227. As will be appreciated, the rotating stop cock 214 may be positioned so that the rotating dosing conduit 238 is in fluid communication with any of the stationary dosing conduits (230, 231, 232, 233, 234, 235, 236, 237) of the various dosing units, depending on which fluid needs to be dosed. Additionally, the stopcock may be positioned to close flow through the dosing conduits. The above design allows for the storage and addition of numerous reagents without the need for several dosing ports on the analytical conduit.

In one embodiment of the invention, the automated analytical apparatus includes a rotary dosing module which includes reagent, diluent, and calibrant dosing units; the sampling unit is provided on the analytical conduit as a separate component that is not integrated into the dosing module.

Figure 11:
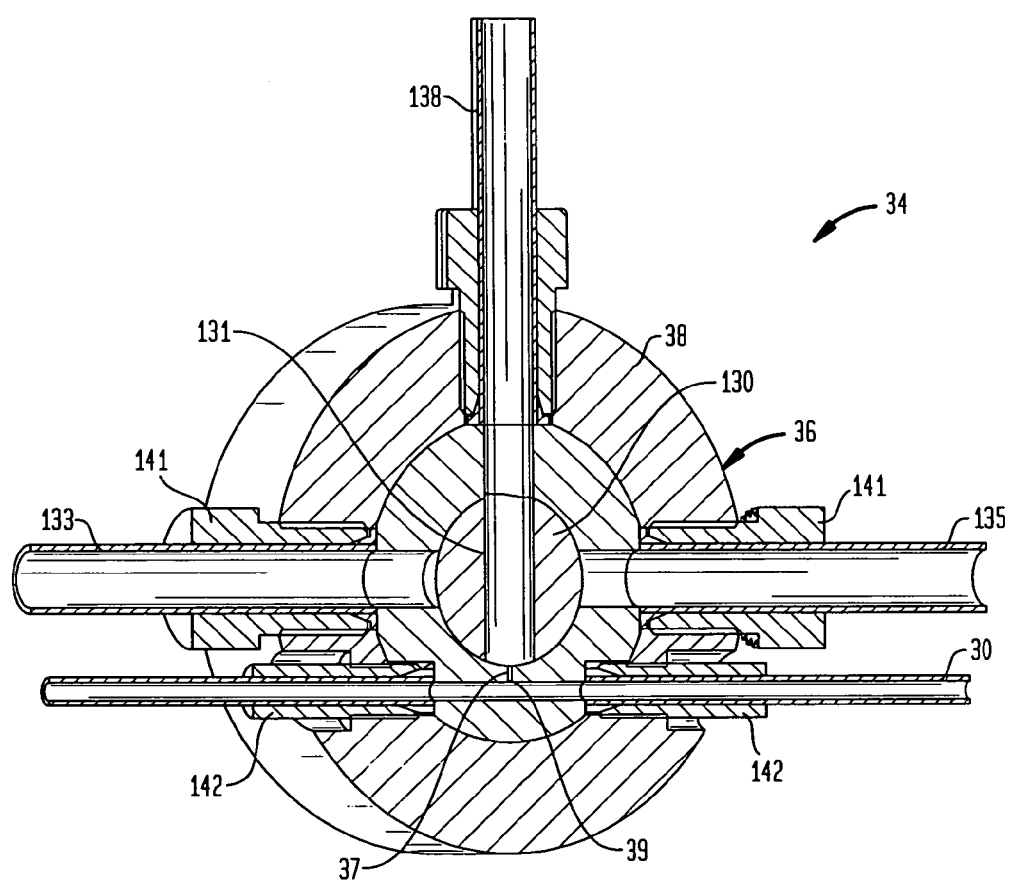
FIG. 11 is a diagram of a dedicated rotary sampling unit suitable for use in the invention.

One design of a sampling unit is shown in FIG. 11. As can be seen therein, the sampling unit 34 is positioned to be in fluid communication with analytical conduit 30. In this embodiment, the sampling unit includes a four-way valve 36 having a housing 38, a sampling conduit 37, a sampling port 39, and a sampling inlet conduit 133 which is coupled to an auxiliary pump (not shown) to provide sample from a sample source. The sampling unit also includes a flushing conduit 135 and a vent conduit 138. The four-way valve 36 includes a rotating stopcock 130 having an enlarged sample conduit segment 131. To illustrate proportions of the apparatus, the sampling conduit 37 may be an approximately 0.02 inch diameter bore, where the enlarged sample conduit segment 131, inlet conduit 133, and flushing conduit 135 may have a diameter of about 0.25 inches. The sample and analytical conduits are conveniently coupled to the rotary sampler by appropriately sized ferrules and threaded nut connectors 141 and 142.

Figure 12A:
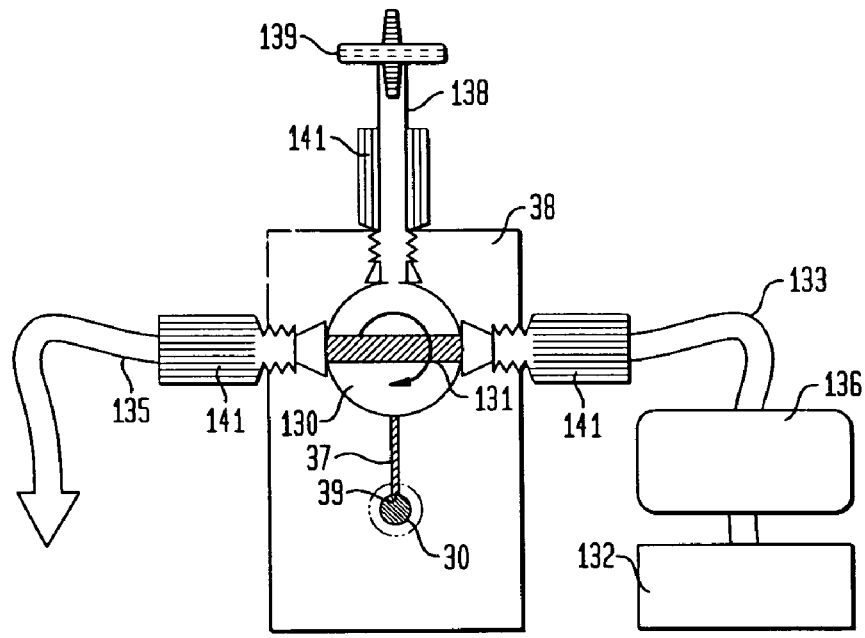
FIGS. 12a and 12b are schematic diagrams illustrating the operation of a rotary sampling unit which is suitable for use with the invention.
Figure 12B:
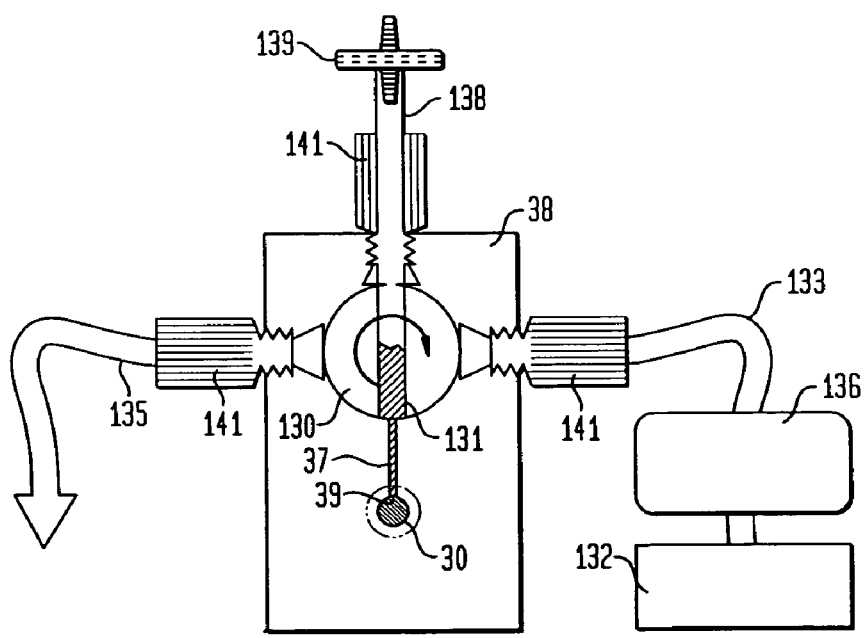

Operation of the sampling unit is illustrated schematically with reference to FIGS. 12a and 12b. To load a sample, the rotating stopcock 130 is rotated such that the enlarged conduit segment 131 is in communication with the inlet conduit 133 and flushing conduit 135, as shown FIG. 12a. A fluid sample from sample source 132 is pumped into the inlet conduit 133 by auxiliary pump 136, through the enlarged sample conduit 131 and out to the flushing conduit 135 where the liquid exits the system. When the sampling unit is adequately flushed, the rotary valve is rotated 90° to the position shown in FIG. 12b; thus, retaining a volume of sample in the enlarged sampling conduit segment 131. The terminus of vent conduit 138 is in open air possibly through a gas permeable filter to exclude particulates, or if needed, in an air-tight gas-sampling bag that can be filled with any gas that is free of the analyte of interest, to prevent contamination of the sample by ambient air. The use of an air-tight bag may be desirable where the ambient air would contaminate the sample; for example, the use of a bag filled with nitrogen gas may be desirable for analyzing ammonia content in a hog farm lagoon, because the ambient air likely also contains ammonia levels which could contaminate the sample. The vent conduit 138 may also include a filter 139 such as a TEFLON®-membrane syringe filter. When the piston on the syringe pump of the analytical apparatus is retracted with the downstream valve 70 closed (not shown in FIGS. 12a and 12b), a portion of the sample will pass from the enlarged sampling conduit 131 through the sampling conduit 37 out of the sampling port 39 and into the analytical conduit 30. Advantageously, the only moving part in this unit is plug 130. The sampling unit may be subsequently flushed as described above by pumping sample out of the flushing conduit 135. The small void volume left in conduit 37 is purged as described above. FIGS. 12a and 12b also show threaded connectors 141 which may be used to connect the various tubing of the conduits together.

Figure 13A:
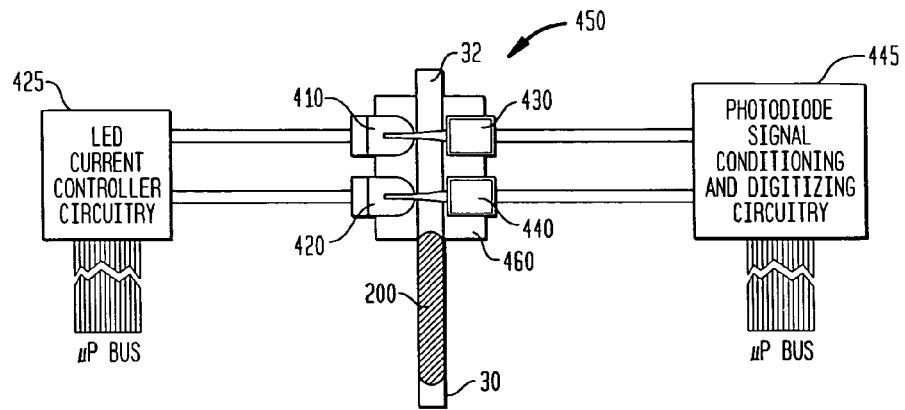
FIGS. 13a and 13b are schematic diagrams of a detector that may be suitable for use in the invention.
Figure 13B:
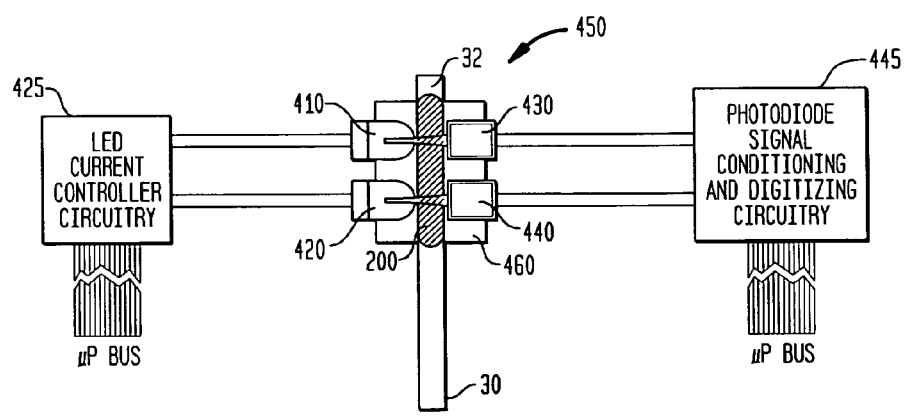

FIG. 13a and 13b illustrate a detector which may be used in connection with the invention. The detection zone 450 includes a machined, black-anodized aluminum or plastic block 460, where the analytical conduit 30 containing system fluid 32, is slip-fitted in the block. The block may be insulated and thermostatted if desired. An LED 410 and reference LED 420 are mounted on the back side of a printed circuit board (PCB) 425 which is coupled to a control system to control the current therethrough. The detection zone also includes a photodiode with filter 430 and a reference photodiode with filter 440. The photodiodes are mounted on a PCB 445 equipped with electronic components for analog signal conditioning e.g. current to voltage conversion, log-ratioing, digitization or direct current to digital conversion with high resolution current-to-digital converters. Various LED's may be used in the detection zone, including those capable of generating 543 nm wavelengths (for Griess reaction nitrite), 660 nm (for salicylate-hypochlorite reaction ammonium determinations), and 880 nm (for phosphoantimonylmolybdenum blue orthophosphate determinations), among others. Here also, the LEDs may be mounted at 90 degrees to the photodiodes to enable fluorescence measurement. The reference LED may generate 1050 nm wavelength near IR radiation, or other wavelengths where light is not substantially absorbed by the analyte or derivitized chromophore of the analyte of interest. In operation, LED intensity across the system fluid is adjusted to an appropriate level (FIG. 13a) before a test bolus is positioned in the detection zone for measurement of percent transmission, absorbance, or fluorescence of the test bolus (FIG. 13b).

Figure 14:
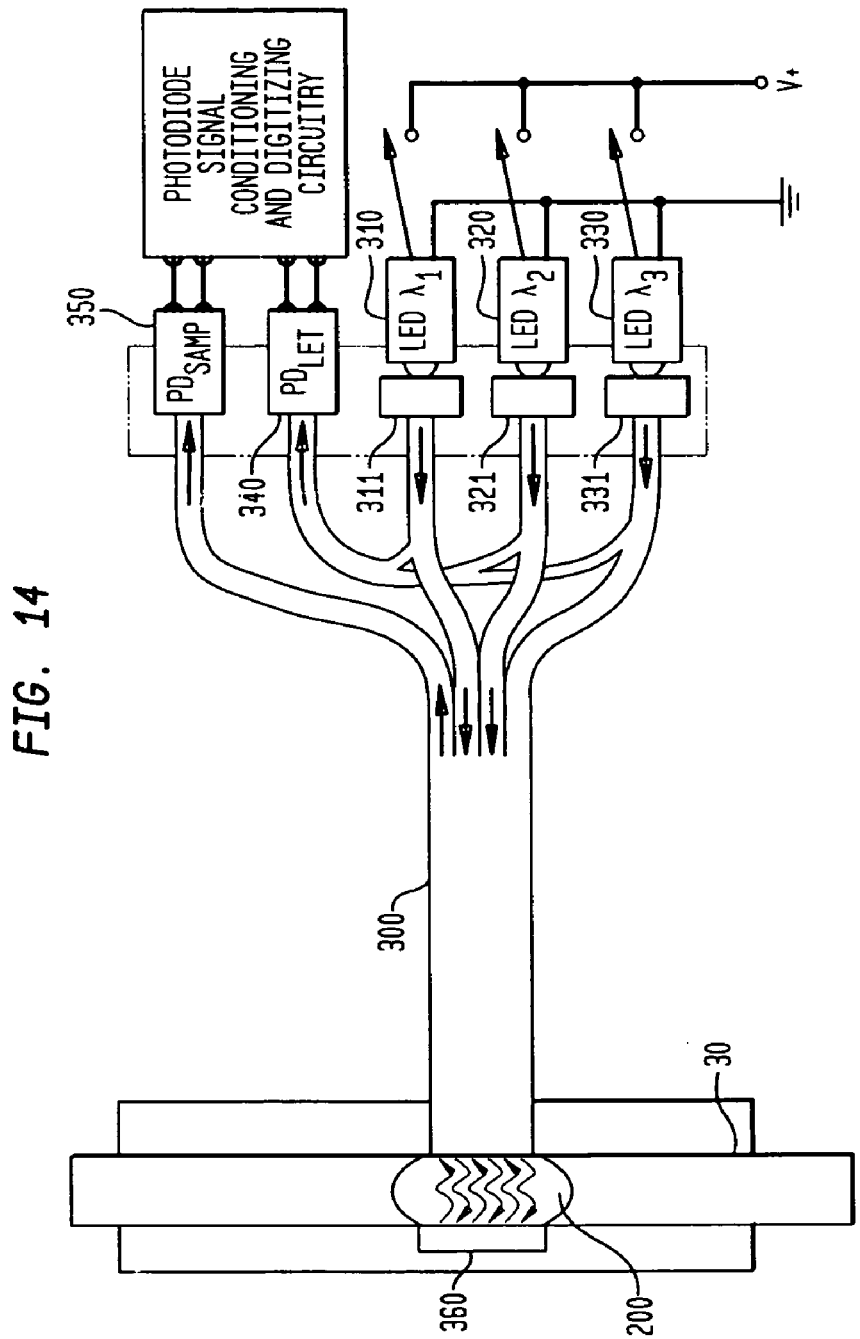
FIG. 14 is a schematic diagram of another embodiment of a detector that may be suitable for use in the invention.

FIG. 14 illustrates another embodiment of a detection system that is suitable for use in the invention, where the system includes a randomized fiber optic bundle 300 including three LED sources 310, 320, and 330 of different wavelength, and three interference filters 311, 321, and 331. Also included is a reference photodiode 340 adapted to detect light directly from the LED sources, and a photodiode detector 350 which is adapted to receive light source that is reflected off of mirror 360 through sample bolus 200. Note that the mirror in FIG. 14 doubles the effective light path through the aqueous test bolus 200 in the analytical conduit 30, theoretically doubling its Beer's Law absorbance per unit concentration. It will also be understood by those skilled in the art that other detector configurations may be used to increase the Beer's Law absorbance of the sample, for example, by measuring absorbance through the longitudinal axis of the bolus (e.g., by forming a bend in the analytical conduit in the detection zone), or by increasing the diameter of the analytical conduit in the detection zone for radial absorbance measurements. In the case of fluorescence detection, a UV LED mounted perpendicularly to the LED in the detection zones of FIGS. 1, 13, and 14 could serve as an excitation source.

While the inventive apparatus and method may be used in any field where wet chemical analysis of liquid samples is required, it has been discovered that the above described apparatus and method are particularly useful for on-site water quality analysis, and specifically for environmental water monitoring. Currently, if wet chemical analysis is needed at environmental sites, technicians travel to the site of interest, collect samples, and send them back to a laboratory for analysis. This procedure is particularly inconvenient and cost prohibitive where it is desired to take a sample, for instance, once per hour or once per day, to measure changes in the water. With the present invention the device may be installed on-site to monitor a water source for analytes such as nutrients (nitrate, nitrite, ammonium, sugars, amino acids, proteins); trace metals (iron, manganese, cadmium); major cations (calcium, magnesium, potassium, and sodium); major anions (chloride, sulfate); nitrogen; phosphorous; chlorophyll content; bacteria content; among others.

The inventive apparatus can also be made submersible for deployment on surface buoys, which increasingly are used for coastal and estuarine nutrient monitoring and other similar applications. Here and in standard shipboard oceanographic survey work, it is also anticipated that the invention can be adapted as a zero-dispersion sampler for water column depth profiling. For example, sample aliquots can be formed at predetermined depths to produce a series of boluses, each comprised of water from that depth. Analyses could be performed while the analyzer is submersed, or after the apparatus is returned to the surface in the case of shipboard application.

The invention is also suitable to monitor industrial and pharmaceutical processes. For example, the apparatus may be used to monitor starting materials and end products in production-scale bioreactors that are increasingly used in the food and pharmaceutical industries. Many pharmaceutical houses use recombinant DNA procedures to induce bacteria and yeasts to produce enzymes and/or pharmaceutically desirable compounds, such as insulin and human growth hormone. For optimum yield, starting materials and nutrients must be monitored throughout the course of fermentation. Thus, the inventive apparatus, may be positioned on the side of a bioreactor (or other reactor) to monitor either a feed stream, product stream, or intermediate stream.

Among various unique features and advantages of the invention, there is enumerated the following:

(1) The apparatus is best described as an automated, fluid-carrier discrete analyzer uniquely distinct from continuous flow or flow-injection analyzers. Unlike prior art devices, aqueous test boluses are formed in the midst of the analytical conduit (rather than at a terminus);

(2) The invention greatly minimizes the number of moving parts and, thus exhibits low maintenance and ease of operation, i.e., it is useable by non-experts;

(3) The method and apparatus are capable of generating and analyzing extremely small test boluses, either singly, or in batches;

(4) The method and apparatus use microliter reagent volumes and therefore generate very little waste. For instance, analyzing 1000 samples, e.g., hourly for 41 days, for a single parameter, the invention would consume only a few milliliters of reagents and generate only about 75 milliliters of waste. This scale of reagent use and waste production is competitive with solid-state sensor technology;

(5) The set-up, configuration, and "plumbing" of the apparatus are extremely simple;

(6) Calibration is automatic and can be accomplished by generating test boluses each containing a different dilution of a stock calibrant;

(7) Time-honored wet chemical methodology is achieved with sensor-like simplicity;

(8) Perfluorohydrocarbon system fluid is inert, nontoxic, immiscible with and denser than water. Its high density makes it easy to separate from aqueous waste for continuous recycling through the analytical conduit;

(9) The number of reagents that can be added successively with reaction periods in between are limited only by the number of dosing units on the dosing module;

(10) No air bubble gaps or vanish zones are required

(11) The apparatus is immune optical window fouling. The analytical conduit, which may also serve as the detector "windows," is isolated from aqueous boluses by the annular film of hydrophobic system fluid that preferentially wets its inner surfaces.

(12) The apparatus can be made at a small size and requires minimal electrical power, which aid in field portability; and

(13) The apparatus has low purchase and maintenance costs.

Additional Embodiments

Additional embodiments of the inventive process and automated analyzer are also contemplated. For example, there is provided in connection with the present invention an apparatus which enables the automated analysis of discrete aqueous samples and includes (a) an elongated analytical conduit with a hydrophobic carrier liquid; (b) a sampling unit configured to form discrete aqueous samples and introduce them into the analytical conduit; (d) a pump system in fluid communication with the analytical conduit and operable to allow alternating direction flow through the transport conduit; d) a reagent dosing unit configured to add a reagent directly to the discrete aqueous sample aliquots, where the dosing unit includes a reagent conduit that is coupled to the analytical conduit, wherein the dosing unit includes a valve positioned on the reagent conduit to control reagent flow therethrough; and e) a detector positioned to measure an analyte in the discrete sample which is in the analytical conduit. The sampling unit may be coupled to the analytical conduit by a sampling conduit which includes a valve positioned thereon, which is operable to stop flow from a sample source to the analytical conduit, and concurrently allow flow to a flushing conduit which directs fluid out of the apparatus.

The apparatus may further include a mixing zone along the analytical conduit which is optionally heated with a heating unit, and where the conduit is coil-shaped.

The apparatus may include a plurality of reagent dosing units, which may be configured to selectively couple to a shared reagent conduit which is in communication with the analytical conduit, whereby flow may be selectively induced from each dosing unit by positioning a rotating valve.

In yet another embodiment there is provided an apparatus for measuring discrete aqueous samples, where the apparatus includes (a) an elongated analytical conduit containing a hydrophobic carrier liquid; (b) a syringe pump coupled to the analytical conduit, and operative to induce fluid flow therein; (c) a sampling unit which is adapted to form a discrete aqueous sample and introduce it into the analytical conduit; (d) a reagent dosing unit having a reagent reservoir to hold reagent, a reagent conduit which is coupled to the reservoir and to the analytical conduit, and a valve positioned on the reagent conduit and adapted to intermittently allow fluid flow between the reagent reservoir and to the analytical conduit; and (e) a detection zone having at least one analytical detector which is positioned on the analytical conduit.

While the invention has been illustrated in connection with several examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. An automated analyzer for discrete sample aliquots with carrier fluid recycle comprising:
   (a) an analytical conduit containing hydrophobic carrier fluid, the conduit and hydrophobic carrier fluid receiving discrete liquid aliquots of predetermined volume which are immiscible with the hydrophobic carrier fluid, such that the discrete aliquots are disposed in the carrier fluid and movable concurrently therewith;
   (b) a selection/recycle valve;
   (c) a hydrophobic carrier fluid recycle reservoir connected to the selection/recycle valve (d) a bidirectional pump connected through the selection/recycle valve to a first location along the analytical conduit, communicating with the hydrophobic carrier fluid and being operable to induce controlled bidirectional flow of the carrier fluid within the analytical conduit in response to a first control signal; the selection/recycle valve alternatively connecting the bidirectional pump with either the analytical conduit or the hydrophobic carrier fluid recycle reservoir such that it is operable to direct the flow of hydrophobic carrier fluid into or out of the pump to or from the analytical conduit or such that it is operable to direct the flow of hydrophobic carrier fluid into or out of the pump to or from the hydrophobic carrier fluid recycle reservoir from which the analytical conduit is replenished with recycled hydrophobic carrier fluid;

(e) a shut-off valve located at a second location along the analytical conduit, communicating with the hydrophobic carrier fluid and being operable to prevent flow of the carrier fluid at said second location of the analytical conduit in response to a second control signal;

(f) a sampling unit communicating with the analytical conduit located between the bidirectional pump and the shut-off valve for providing discrete liquid aliquots to the analytical conduit;

(g) a dosing unit located at a third location along the analytical conduit, the third location being intermediate said first location of the pump and the second location of the shut-off valve, and the dosing unit having a reagent feed valve connected to a reagent containing reservoir, the reagent feed valve being disposed between the reagent containing reservoir and the analytical conduit such that the reagent containing reservoir communicates with the analytical conduit through the reagent feed valve to supply fluid from the reagent-containing reservoir to discrete liquid aliquots disposed in the analytical conduit, wherein the reagent feed valve is responsive to a third control signal;

(h) a controller providing the first, second and third control signals respectively to the pump, the shut-off valve, and the feed valve of the dosing unit, whereby the controller, pump, shut-off valve and carrier fluid are operable to position discrete liquid aliquots at predetermined locations along the analytical conduit, and whereby the pump may be used to draw fluid from the reagent containing reservoir of the dosing unit and supply it to the discrete liquid aliquots upon concerted operation of the pump, shut-off valve, and feed valve; and (i) a detector located at a fourth position with respect to the analytical conduit and operable to detect an analyte in a discrete liquid aliquot positioned at the fourth position.

2. The automated analyzer according to claim 1, wherein the pump is a syringe pump.

3. The automated analyzer according to claim 1, wherein the discrete liquid aliquots have a volume in the range of from 1 to 100 microliters.

4. The automated analyzer according to claim 1, wherein the discrete liquid aliquots have a volume in the range of from 5 to 50 microliters.

5. The automated analyzer according to claim 1, wherein the discrete liquid aliquots have a volume in the range of from 10 to 30 microliters.

6. The automated analyzer according to claim 1, wherein the discrete liquid aliquots have a volume in the range of from 500 microliters to 5,000 microliters.

7. The automated analyzer according to claim 1, wherein the hydrophobic carrier fluid includes a perfluorohydrocarbon fluid.

8. The automated analyzer according to claim 1, wherein the analytical conduit has an interior wall comprising a fluorocarbon polymer.

9. The automated analyzer according to claim 1, wherein the detector is a photometric detector.

10. The automated analyzer according to claim 1, wherein the detector is a fluorescence detector.

11. The automated analyzer according to claim 1, wherein the detector is a UV detector.

12. The automated analyzer according to claim 1, wherein the detector includes one or more of an ultraviolet, visible light, or infrared emitting diode component.

13. The automated analyzer according to claim 1, wherein the cross-sectional area of the analytical conduit is substantially uniform over its length.

14. The automated analyzer according to claim 1, wherein the controller is a microprocessor control system.

15. A method of sampling a water source, said method comprising the steps of:

(a) providing an analytical conduit containing hydrophobic carder fluid, said conduit being also receiving discrete sample aliquots from the water source which communicates therewith through a feed valve of a sampling unit as hereinafter provided;

(b) providing a pump responsive to a first control signal and connected at a first position along the analytical conduit, communicating with the hydrophobic carrier fluid and being operable to induce controlled flow of the carrier fluid;

(c) providing a shut-off valve responsive to a second signal and located at a second position along the analytical conduit, communicating with the hydrophobic carder fluid and being operable to prevent flow of the carrier fluid;

(d) providing a sampling unit located at a third location along the analytical conduit, the third location being intermediate said first location of the pump and the second location of the shut-off valve, said sampling unit being in communication with the water source and operative to dispense water sample aliquots through a sampling feed valve to the analytical conduit; and (e) providing a reagent dosing unit located along the analytical conduit, the location of the dosing unit being intermediate said first location of the pump and the second location of the shut-off valve, and the dosing unit having a reagent feed valve and the reagent containing reservoir, the reagent feed valve being disposed between the reagent containing reservoir and the analytical conduit such that the reagent containing reservoir communicates with the analytical conduit through the reagent feed valve to supply fluid from the reagent-containing reservoir to discrete liquid aliquots disposed in the analytical conduit, wherein the reagent feed valve is responsive to a third control signal;

(f) controlling the pump, the shut-off valve, the feed valve of the sampling unit to draw a discrete sample aliquots of predetermined volume from the water source into the analytical channel, such that the discrete sample aliquots is are disposed it the hydrophobic carrier fluid.

16. The method according to claim 15, wherein the first, second, and third control signals are distinct.

17. The method according to claim 15, wherein the discrete sample aliquots of predetermined volume are drawn into the analytical conduit by concurrently closing the shut-off valve, opening the feed valve of the sampling unit, and controlling the pump to induce fluid flow in the conduit in the direction toward said first position.

18. An automated analyzer for discrete sample aliquots with carrier fluid recycle comprising:
  (a) an analytical conduit containing hydrophobic carrier fluid, the conduit and hydrophobic carrier fluid receiving discrete liquid aliquots of predetermined volume which are immiscible with the hydrophobic carrier fluid, such that the discrete aliquots are disposed in the carrier fluid and movable concurrently therewith;
  (b) a selection/recycle valve;
  (c) a hydrophobic carrier fluid recycle reservoir connected to the selection/recycle valve;
  (d) a bidirectional pump connected through the selection/recycle valve to a first location along the analytical conduit, communicating with the hydrophobic carrier fluid and being operable to induce controlled bidirectional flow of the carrier fluid within the analytical conduit in response to a first control signal; the selection/recycle valve alternatively connecting the bidirectional pump with the analytical conduit or the hydrophobic recycle reservoir such that it is operable to direct the flow of hydrophobic carrier fluid into or out of the pump to or from the analytical conduit or such that it is operable to direct the flow of hydrophobic carrier fluid into or out of the pump to or from the hydrophobic carrier fluid recycle reservoir from which the analytical conduit is replenished with recycled hydrophobic carrier fluid;
  (e) a shut-off valve located at a second location along the analytical conduit, communicating with the hydrophobic carrier fluid and being operable to prevent flow of the carrier fluid at said second location of the analytical conduit in response to a second control signal;
  (f) a sampling unit communicating with the analytical conduit and a sample source located between the bidirectional pump and the shut-off valve for providing discrete liquid aliquots to the analytical conduit; said sampling unit being provided with a sampling unit purge system having an auxiliary pump communicating with a sampling valve and a purge outlet, the purge outlet being constructed and arranged to exhaust purge fluid externally to the automated analyzer such that purge fluid is not accumulated in the recycle reservoir;
  (g) a dosing unit located at a third location along the analytical conduit, the third location being intermediate said first location of the pump and the second location of the shut-off valve, and the dosing unit having a reagent feed valve and a reagent containing reservoir, the reagent feed valve being disposed between the reagent containing reservoir and the analytical conduit such that the reagent containing reservoir communicates with the analytical conduit through the reagent feed valve to supply fluid from the reagent-containing reservoir to discrete liquid aliquots disposed in the analytical conduit, wherein the reagent feed valve is responsive to a third control signal;
  (h) a controller providing the first, second and third control signals respectively to the pump, the shut-off valve, and the feed valve of the dosing unit, whereby the controller, pump, shut-off valve and carrier fluid are operable to position discrete liquid aliquots at predetermined locations along the analytical conduit, and whereby the pump may be used to draw fluid from the reagent containing reservoir of the dosing unit and supply it to the discrete liquid aliquots upon concerted operation of the pump, shut-off valve, and feed valve; and
  (i) a detector located at a fourth position with respect to the analytical conduit and operable to detect an analyte in a discrete liquid aliquot positioned at the fourth position.

19. The automated analyzer according to claim 1, wherein the hydrophobic carrier fluid is inert.

\* \* \* \* \*